United States Patent [19]

Shlenker

[11] Patent Number: 4,919,966
[45] Date of Patent: Apr. 24, 1990

[54] COVERING SUCH AS A GLOVE, CONDOM OR SHEATH FOR INHIBITING THE SPREAD OF CONTAGIOUS DISEASES AND METHODS OF MAKING AND USING THE SAME

[76] Inventor: Robin R. T. Shlenker, 2165 E. Alameda Ave., Denver, Colo. 80209

[21] Appl. No.: 143,184

[22] Filed: Jan. 13, 1988

Related U.S. Application Data

[63] Continuation-in-part of Ser. No. 74,679, Jul. 17, 1987, Pat. No. 4,771,482.

[51] Int. Cl.$^5$ .................... A01N 1/02; A41D 19/00
[52] U.S. Cl. ............................................ 427/2; 2/159; 2/161 R; 2/168; 128/844; 604/349; 604/353
[58] Field of Search ................... 128/844; 427/2; 604/349, 353; 2/159, 161 R, 168

[56] References Cited

U.S. PATENT DOCUMENTS

| | | | |
|---|---|---|---|
| 1,954,262 | 4/1934 | Potter | 2/159 |
| 2,410,460 | 11/1946 | Robinson | 128/294 |
| 2,586,674 | 2/1952 | Lonne | 128/294 |
| 2,792,835 | 5/1957 | Ferguson | 128/260 |
| 3,110,035 | 11/1963 | La Hue | 2/168 |
| 3,121,877 | 2/1964 | Gintner | 2/159 |
| 3,342,182 | 9/1967 | Charos | 2/161 X |
| 3,633,216 | 1/1972 | Schonholtz | 2/168 |
| 3,672,351 | 6/1972 | Ubersax | 2/168 X |
| 3,911,501 | 10/1975 | Seltzer | 2/167 |
| 3,975,775 | 8/1976 | Alsop | 2/163 |
| 4,185,330 | 1/1980 | Stager | 2/167 X |
| 4,214,321 | 7/1980 | Nuwayser | 2/167 |
| 4,432,357 | 2/1984 | Pomeranz | 604/349 X |
| 4,446,860 | 5/1984 | Gutnick | 604/328 X |
| 4,471,538 | 9/1984 | Pomeranz et al. | 2/159 X |
| 4,771,482 | 9/1988 | Shlenker | 2/161 R |

FOREIGN PATENT DOCUMENTS 540241 10/1941 United Kingdom .

OTHER PUBLICATIONS

Plastics Fabrication and Uses, vol. 74, 1971.
Chemical Abstracts, vol. 78, 1973.
Nuclear Technology, vol. 80, 1974.
Cumulated Index, 1983.

*Primary Examiner*—Michael Lusignan

[57] ABSTRACT

A covering such as a glove, condom or sheath for inhibiting the spread of contagious diseases such as AIDS and Hepatitis to a person contacting the body fluid of a person infected with the disease. The covering is flexible, stretchable, and relatively thin, and includes at least one relatively thin layer of material containing a sterilizing fluid capable of sterilizing the microbes that produce the disease. If an object cuts through the covering and into a person's skin, the sterilizing fluid will be released to help sterilize the infectious microbes in the region around the cut so that the microbes are rendered ineffective either before reaching the person's skin, after reaching the person's skin, or both. Various methods of making and using the covering are also disclosed.

86 Claims, 2 Drawing Sheets

COVERING SUCH AS A GLOVE, CONDOM OR SHEATH FOR INHIBITING THE SPREAD OF CONTAGIOUS DISEASES AND METHODS OF MAKING AND USING THE SAME

BACKGROUND OF THE INVENTION

This patent application is a continuation-in-part of U.S. patent application Ser. No. 074,629, filed on July 17, 1987 now U.S. Pat. No. 4,771,482, patented Sept. 10, 1988, for "Glove For Inhibiting The Spread Of Contagious Diseases And Method Of Using The Same", which is also owned by the same applicant.

There are a number of contagious diseases that can be spread by passing infectious agents or microbes from one person's blood or other infective body fluid to another person's blood or other body fluid. Two of the most feared diseases that can be spread in this manner are Hepatitis and Acquired Immunodeficiency Syndrome, otherwise known as AIDS. Often, one must touch, handle or otherwise come in contact with a person's body fluid either knowing that the person has a disease such as AIDS or without an opportunity to adequately determine whether the person has such a disease. For example, doctors and nurses must treat patients and perform surgical operations on patients sometimes knowing that the person has a contagious disease or during an emergency situation when there is no opportunity to determine whether the person has such a disease. Similarly, policemen and ambulance workers must often handle and treat persons involved in automobile accidents, shootings, and the like without an opportunity for determining whether the person has a contagious disease. Also, persons may desire sexual intercourse without knowing whether their sex partner possesses a sexually transmittable disease such as AIDS.

Doctors, dentists, medical technologists, and nurses protect against the transmission of contagious diseases in the work place and during invasive procedures by wearing conventional flexible, stretchable, disposable, sterile latex gloves. Such latex gloves are usually powdered on the inside with talc or a similar material to help keep the glove interior dry and to facilitate removal of the glove. A decision was recently made to equip the Denver, Colo. police force with such latex gloves so that policemen could use the gloves in situations where they could contact another person's body fluids, such as at car accidents and shootings. While these conventional latex gloves provide a great degree of protection against the transmission of contagious diseases, such gloves can be torn, ripped, punctured or otherwise cut. The person's hand is often correspondingly cut immediately below the cut in the glove. For example, doctors often cut their fingers and hands with a scalpel during operations and sometimes puncture their fingers and hands with suture needles. Also, policemen might cut their hands on pieces of glass, jagged pieces of metal, and the like at car accident scenes. The frequency of such cuts is significant, and, when considering the fear of accidentally contracting diseases such as AIDS, constitutes a serious problem.

Although the use of conventional latex condoms and other condoms have been touted as a sure prevention against sexually transmitted diseases, recent newspaper articles have reported studies that seriously question the degree of such prevention, and of course, condoms that are punctured do not provide the desired degree of protection. Thus, conventional latex condoms do not provide the desired degree of protection against sexually transmitted diseases such as AIDS.

SUMMARY OF THE INVENTION

The present invention relates to a covering such as a glove, condom or sheath for inhibiting the spread of a contagious disease such as AIDS and Hepatitis to a person contacting the body fluid of a person infected with the disease. The covering is flexible, stretchable, and relatively thin, and includes at least one relatively thin layer of material containing a fluid capable of sterilizing the microbes that produce the disease. If an object cuts through the covering and into a person's skin, the sterilizing fluid will be released to help sterilize the infectious microbes in the region around the cut so that the microbes are rendered ineffective either before reaching the person's skin, after reaching the person's skin, or both. Also, to the extent that the microbes might traverse the covering such as during sexual intercourse the sterilizing fluid will render them ineffective. Various methods of making and using the covering are also disclosed.

BRIEF DESCRIPTION OF THE DRAWINGS

The invention will be described with reference to the accompanying drawings, wherein.

DESCRIPTION OF THE PREFERRED EMBODIMENT

Figure 1:
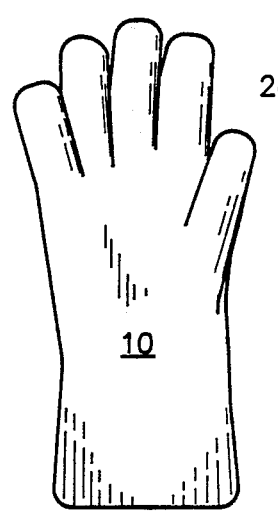
FIG. 1 is a plan view of a covering in the form of a glove in accordance with one embodiment of the present invention.

Referring now to the drawings wherein like reference numerals and symbols refer to the same item, there is shown in FIG. 1 a covering in the form of a glove 10 having a shape and configuration similar in all essential respects to the conventional latex gloves presently worn by doctors, dentists, and nurses. An example of a conventional latex glove is the "Perry" surgeon's glove manufactured by Smith & Nephew of Massillon, Ohio. The glove 10 of the present invention, however, possesses at least one pocket or chamber containing a fluid capable of sterilizing contagious disease-producing microbes.

Figure 4:
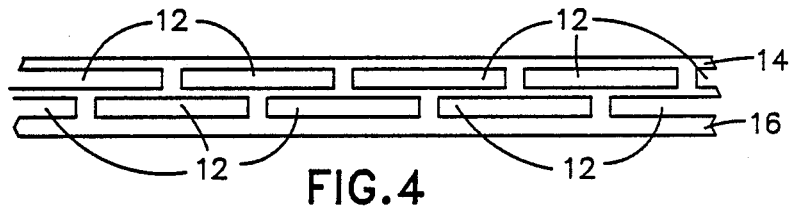
FIG. 4 is a schematic cross-sectional view of the gloves shown in FIGS. 1, 2 and 3 revealing two layers of chambers containing a sterilizing fluid.
Figure 5:
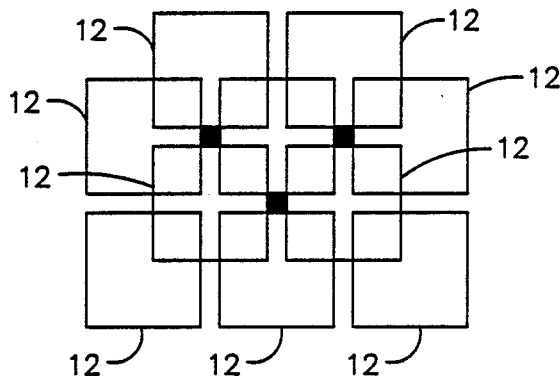
FIG. 5 is a top schematic illustration showing the staggered relation of the chambers in the two layers revealed in FIG. 4.

As best shown in FIGS. 4 and 5, the glove 10 as well as the other forms of coverings of the present invention may include an array of thin, square-shaped chambers 12 arranged side by side in two layers. The chambers 12 in each layer are staggered with respect to the chambers 12 in the adjacent layer. Such staggering minimizes the possibility that a needle or similar object could puncture through the glove 10 and cut the person's hand without protruding through one of the chambers 12 and releasing the sterilizing fluid contained therein. As shown by the darkened areas in FIG. 5, the staggered arrangement of the two layers of chambers 12 results in a relatively minuscule potential area for a needle or similar object to puncture through the glove 10 and cut the person's hand without also puncturing the cavity 12. It should be readily appreciated that either a single layer of chambers 12 could be utilized or three layers of chambers 12 arranged in a staggered relationship could be effectively used and would insure that a needle or similar object could not puncture through the glove 10 and cut a person's hand without also puncturing a chamber 12. Also, although FIGS. 4 and 5 depict relatively thin, square-shaped chambers 12, a variety of different shapes and sizes of chambers 12 can be effectively used. For example, the chambers 12 might be relatively thin and circular shaped or diamond shaped. Moreover, although FIG. 4 depicts the chambers 12 as possessing squared or cornered ends, it should be appreciated that the ends may be curved or rounded.

The thickness of the glove 10 is preferably in the range of between one millimeter and five millimeters so that the flexibility and stretchability of the glove can be maintained and so that the glove 10 does not significantly diminish the sensitivity with which the person's hand touches and feels an object. Also, the outer sheath 14 of the glove 10 (that region of the glove disposed outwardly of the outer layer of chambers 12) is relatively thinner than the inner sheath 16 of the glove 10 (that region of the glove located inwardly of the inner layer of chambers 12). The relative thickness of the sheath 16 provides strength so that the inner sheath 16 might not be cut even though the outer sheath 14 is cut. A glove 10 constructed according to the depictions of FIGS. 4 and 5 preferably contains between 50 and 500 different chambers 12. Preferably the volume of each chamber is less than two cubic centimeters.

Figure 6:
FIG. 6 is a schematic cross-sectional view of a covering according to an embodiment of the present invention.

A glove 10 as well as the other forms of coverings of the present invention can also be constructed somewhat like a sponge, with a plurality of tiny voids or chambers 17 that encapsulate the sterilizing fluid. Such a glove 10 construction is depicted in FIG. 6. Again, it should be appreciated that it would be virtually impossible to puncture through a glove 12 constructed with a host of chambers 17 encapsulating the sterilizing fluid without also puncturing at least one of the chambers 17. In the embodiment depicted in FIG. 6, there are preferably at least 500 chambers 17 throughout the glove 10, and the volume of each chamber 17 is preferably less than one cubic millimeter. The sponge-like material may be sealed by causing its surfaces to melt and then harden to form a uniform, continuous, non-porous barrier. In a variation of the embodiment depicted in FIG. 6, the sponge-like material may be saturated with sterilizing fluid and then sealed on both sides with a plastic coating, a latex coating or similar coating. Such coating may be applied by dipping the saturated, sponge-like material in a vat of liquid plastic which quickly solidifies or by spraying a liquid plastic onto such material, which also quickly solidifies.

Figure 2:
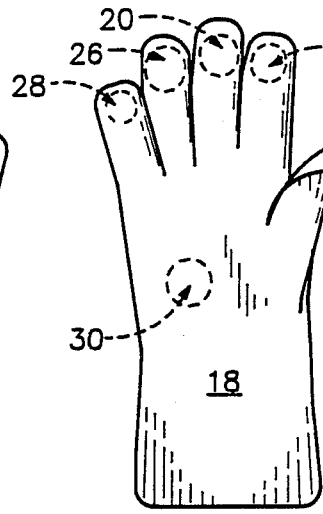
FIG. 2 is a plan view of a covering in the form of a glove according to another embodiment of the present invention depicting areas near the glove fingertips that are devoid of any sterilizing fluid.

The glove 18 shown in FIG. 2 may in all respects be similar to the glove 10 shown in FIG. 1 except that certain regions of the glove 18 are devoid of any chambers 12 containing sterilizing fluid so that sensitivity may be maximized in those regions. Specifically, region 20 on the inside tip of the middle finger, region 20 on the inside tip of the index finger, and region 24 on the inside tip of the thumb are all devoid of chambers 12. It will be appreciated that these regions are most often used by doctors during surgery, especially for grasping a scalpel. Alternatively, regions 26, 28 on the inside tip of the ring finger and the little finger, respectively, as well as a region 30 at the heel of the hand (where the heel of a scalpel contacts the hand) may also be devoid of chambers 12 so that only a very thin layer of latex is covering those areas.

Figure 3:
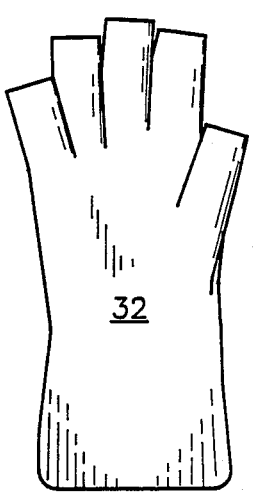
FIG. 3 is a covering in the form of a glove according to yet another embodiment of the present invention in which the glove fingertips have been eliminated.

The glove 32 shown in FIG. 3 is in all respects similar to the glove 10 shown in FIG. 1 except that the fingertips and thumb tip of the glove 3 have been eliminated. The glove 32 is especially suited to be worn over a conventional latex glove. Again, the glove 32 helps maximize the sensitivity in those regions of the person's hand used to touch and feel objects.

Although the glove 10 has been described as being fashioned from latex, the present invention contemplates the glove 10 being fashioned from plastics and possibly other materials.

Figure 7:
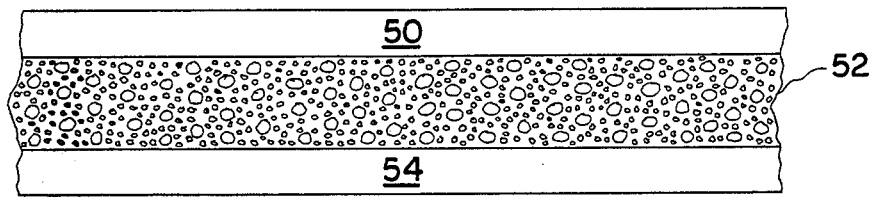
FIG. 7 is a schematic cross-sectional view of a covering according to another embodiment of the present invention.

There is shown in FIG. 7 a covering comprising an outer layer 50 of latex, plastic or other suitable material, an intermediate layer 52, and an inner layer 54, which also may be fashioned of latex, plastic or other material. The intermediate layer 52 may be formed of a sponge-like material with a plurality of tiny voids of chambers that encapsulate the sterilizing fluid, in all respects similar to the construction depicted in FIG. 6. The intermediate layer 52 is "sandwiched" between the outer layer 50 and the inner layer 54. It will be appreciated that the outer layer 50 and the inner layer 54 help insure that the sterilizing fluid does not seep from the intermediate layer 52. Also, it will be appreciated that the tiny voids or chambers within the intermediate layer 52 help insure that the sterilizing fluid does not significantly flow due to gravity or other forces, which would produce bulges of excessive sterilizing fluid as well as regions of insufficient sterilizing fluid.

Figure 8:
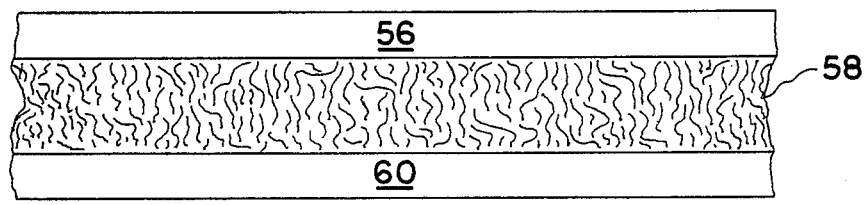
FIG. 8 is a schematic cross-sectional view of a covering according to yet another embodiment of the present invention.

There is shown in FIG. 8 another covering construction according to the present invention comprising an outer layer 56 in all respects similar to the outer layer 50 shown in FIG. 7, an intermediate layer 58, and an inner layer 60 in all respects similar to the inner layer 54 depicted in FIG. 7. The intermediate layer 58 comprises a material that absorbs the sterilizing fluid. Thus, the sterilizing fluid may saturate the region between the outer layer 56 and the inner layer 60 and will not significantly flow in response to gravity or other forces. The intermediate layer 58 may be formed of cellulose (e.g., paper), natural fiber (e.g., cotton) or synthetic fibers in either woven or unwoven condition.

Figure 9:
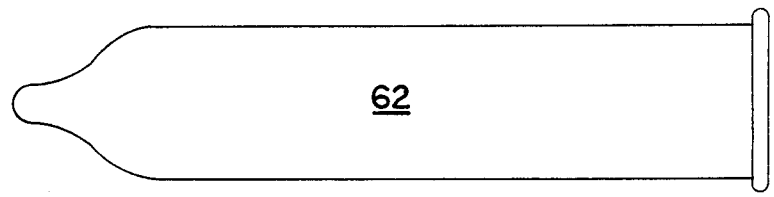
FIG. 9 is a side view of a condom according to an embodiment of the present invention.

The covering embodiments shown in FIGS. 8 and 9 may be formed by saturating the intermediate layer with the sterilizing fluid and then forming the outer and inner layers by dipping the saturated intermediate layer in a vat of liquid plastic, latex or similar coating material which quickly solidifies or by spraying a liquid plastic, latex or similar coating material onto the saturated intermediate layer, which also quickly solidifies.

FIG. 9 depicts a condom 62 in accordance with the present invention. The condom 62 may be constructed with the chambers depicted in FIG. 4 and 5, with the sponge-like material depicted in FIG. 6, with the "sandwiched" construction depicted in FIG. 7, or with the "sandwiched" construction shown in FIG. 8. Such construction may extend preferably throughout substantially the entire condom 62. Alternatively, such construction may comprise only the head or tip of the condom 62.

The covering of the present invention may also include a dual layered sheath or glove formed by inserting one conventional latex glove within a second conventional latex glove which is of virtually identical shape and dimensions. Before the first glove is inserted into the second glove, the sterilizing fluid is applied over the outer surface of the first glove. Such application can be accomplished by spraying the sterilizing fluid onto the glove, brushing the sterilizing fluid onto the glove, sprinkling the sterilizing fluid onto the glove, or dipping the glove into a vat of sterilizing fluid. Moreover, the sterilizing fluid may be in a molten state at a relatively elevated temperature when applied to the glove and then solidified in a layer around the glove.

The sterilizing fluid used in the present invention may comprise a variety of different chemicals and chemical mixtures that are effective in immediately sterilizing contagious disease producing microbes (such as viruses, bacteria and possibly spores) upon contact. In the context of the present invention, the concept of immediate sterilization means that the disease producing characteristic is rendered ineffective within ten minutes, and preferably within thirty seconds. The disease-producing characteristic can be rendered ineffective by killing the microbe, preventing reproduction of the microbe, or otherwise. In those situations where a patient or other person is known to be infected with a particular disease, the sterilizing fluid can be tailored to provide maximum effectiveness in sterilizing the microbes producing that disease. Otherwise, a more general sterilizing fluid such as a bleach solution or a detergent should be used. Also, it should be appreciated that the sterilizing fluid may be in the form of a liquid, gel, paste or powder. Care should be taken to insure that the sterilizing fluid will not react with the material from which the covering is fashioned in such a way as to cause the sterlizing fluid to leak before the covering is normally used.

Some effective sterilizing fluids are:

| Chemical Compound | Known Minimum Concentration By Volume For Immediately Sterilizing AIDS Virus (HIV-1) | Known Minimum Concentration By Volume For Immediately Sterilizing Hepatitis B Virus |
|---|---|---|
| Ethyl Alcohol | 50% | 80% |
| Isopropyl Alcohol | 30% | 70% |
| NP-40 (ethylphenyl-polyethylene glycol) | 1% | — |
| Hydrogen Peroxide | 0.3% | — |
| Household Bleach | 0.1% | 10% |

Although particular embodiments of the present invention have been described and illustrated herein, it should be recognized that modifications and variations may readily occur to those skilled in the art and that such modifications and variations may be made without departing from the spirit and the scope of my invention. Consequently, my invention as claimed below may be practiced otherwise than is specifically described above.

I claim:

1. A covering for inhibiting the spread of a contagious disease to a person contacting the body fluid of a person infected with the disease, said covering adapted to cover at least a portion of at least one extremity of one of the persons, said covering possessing a first array of chambers arranged substantially side by side in a first substantially uniform layer and a second array of chambers arranged substantially side by side in a second substantially uniform layer, said first layer substantially immediately adjacent to and below said second layer, and said chambers of said first array arranged in a staggered relation relative to said chambers of said second array, said chambers containing a sterilizing fluid capable of substantially immediately sterilizing the microbes causing said disease substantially upon contact.

2. A covering according to claim 1 wherein said covering comprises a condom.

3. A covering according to claim 2 wherein said chambers extend substantially only throughout the head or tip region of said condom.

4. A covering according to claim 2 wherein the thickness of said covering is substantially in the range of one millimeter to five millimeters.

5. A covering according to claim 2 wherein said chambers number substantially in the range of between fifty and five hundred.

6. A covering according to claim 5 wherein the volume of substantially each said chamber is less than two cubic centimeters.

7. A covering according to claim 2 fashioned of a flexible, stretchable material.

8. A covering according to claim 2 comprising an outer sheath and an inner sheath adapted to be disposed immediately adjacent to the person's skin, said array of chambers being interposed between said outer sheath and said inner sheath, the thickness of said outer sheath being thinner than the thickness of said inner sheath.

9. A covering according to claim 2 wherein said sterilizing fluid is capable of substantially immediately sterilizing microbes that cause Acquired Immunodeficiency Syndrome (AIDS).

10. A covering for inhibiting the spread of a contagious disease to a person contacting the body fluid of a person infected with the disease, said covering adapted to cover at least a portion of at least one extremity of one of the persons, said covering comprising a sponge-like layer of material possessing a plurality of chambers numbering at least two hundred and wherein the volume of substantially each said chamber is less than two cubic millimeters, said chambers containing a sterilizing fluid capable of substantially immediately sterilizing the microbes causing the disease.

11. A covering according to claim 10 said covering comprises a condom.

12. A covering according to claim 10 further comprising an outer sheet and an inner sheet and wherein said sponge-like layer is disposed intermediate and adjacent to said outer sheet and said inner sheet, said outer sheet and said inner sheet adapted to substantially retain said sterilizing fluid within said sponge-like layers.

13. A covering according to claim 12 wherein said covering comprises a condom.

14. A covering according to claim 12 wherein said covering comprises a glove.

15. A covering according to claim 12 wherein said outer sheet and said inner sheet each comprise latex.

16. A covering according to claim 12 wherein said covering is flexible and stretchable.

17. A covering according to claim 11 wherein said chambers extend substantially only throughout the head or tip region of said condom.

18. A covering according to claim 13 wherein said chambers extend substantially only throughout the head or tip region of said condom.

19. A covering according to claim 11 wherein said sterilizing fluid is capable of substantially immediately sterilizing microbes that cause AIDS.

20. A covering according to claim 13 wherein said sterilizing fluid is capable of substantially immediately sterilizing microbes that cause AIDS.

21. A covering according to claim 10 wherein the thickness of said covering is substantially in the range of one millimeter to five millimeters.

22. A covering according to claim 12 wherein the thickness of said covering is substantially in the range of one millimeter to five millimeters.

23. A covering for inhibiting the spread of a contagious disease to a person contacting the body fluid of a person infected with the disease, said covering adapted to cover at least a portion of at least one extremity of one of the persons, said covering comprising an outer sheet, an intermediate layer of flexible, absorbent material, and an inner sheet, said intermediate layer substantially saturated with a sterilizing fluid capable of substantially immediately sterilizing the microbes causing the disease, said intermediate layer disposed intermediate and adjacent to said outer sheet and said inner sheet, said outer sheet and said inner sheet adapted to substantially retain said sterilizing fluid within said intermediate layer.

24. A covering according to claim 23 wherein said covering comprises a condom.

25. A covering according to claim 23 wherein said covering comprises a glove.

26. A covering according to claim 23 wherein said intermediate layer comprises a woven material.

27. A covering according to claim 23 wherein said intermediate layer comprises cotton.

28. A covering according to claim 23 wherein said intermediate layer comprises cellulose.

29. A covering according to claim 23 wherein said intermediate layer comprises a synthetic fiber.

30. A covering according to claim 23 wherein said outer sheet and said inner sheet each comprise latex.

31. A covering according to claim 23 wherein said covering is flexible and stretchable.

32. A covering according to claim 24 wherein said intermediate layer extends substantially only throughout the head or tip region of said condom.

33. A covering according to claim 24 wherein said sterilizing fluid is capable of substantially immediately sterilizing microbes that cause AIDS.

34. A covering according to claim 23 wherein the thickness of said covering is substantially in the range of one millimeter to five millimeters.

35. A method of inhibiting the spread of a contagious disease to a person contacting the body fluid of a person infected with the disease comprising the steps of:
providing a covering adapted to cover at least a portion of at least one extremity of one of the persons, said covering comprising a sponge-like layer of material possessing a plurality of chambers numbering at least two hundred and wherein the volume of substantially each chamber is less than two cubic millimeters, said chambers containing a sterilizing fluid capable of substantially immediately sterilizing the microbes causing the disease; and
covering at least a portion of the extremity with said cover.

36. A method of inhibiting the spread of a contagious disease according to claim 35 wherein said covering comprises a condom.

37. A method of inhibiting the spread of a contagious disease according to claim 35 wherein said covering comprises a glove.

38. A method of inhibiting the spread of a contagious disease according to claim 35 wherein said covering further comprises an outer sheet and an inner sheet and wherein said sponge-like layer is disposed intermediate and adjacent to said outer sheet and said inner sheet, said outer sheet and said inner sheet adapted to substantially retain said sterilizing fluid within said sponge-like layer.

39. A method of inhibiting the spread of a contagious disease according to claim 38 wherein said covering comprises a condom.

40. A method of inhibiting the spread of a contagious disease according to claim 38 wherein said covering comprises a glove.

41. A method of inhibiting the spread of a contagious disease to a person contacting the body fluid of a person infected with the disease comprising the steps of:
providing a covering adapted to cover at least a portion of at least one extremity of one of the persons, said covering comprising an outer sheet, an intermediate layer of flexible, absorbent material, and an inner sheet, said intermediate layer substantially saturated with a sterilizing fluid capable of substantially immediately sterilizing the microbes causing the disease, said intermediate layer disposed intermediate and adjacent to said outer sheet and said inner sheet, said outer sheet and said inner sheet adapted to substantially retain said sterilizing within said intermediate layer.

42. A method of inhibiting the spread of a contagious disease according to claim 41 wherein said covering comprises a condom.

43. A method of inhibiting the spread of a contagious disease according to claim 41 wherein said covering comprises a glove.

44. A method of making a covering for inhibiting the spread of a contagious disease comprising the steps of:
providing a layer of sponge-like material possessing a plurality of chambers numbering at least two hundred and wherein the volume of substantially each chamber is less than two cubic millimeters;
providing a sterilizing fluid capable of substantially immediately sterilizing the microbes causing the disease;
applying the sterilizing fluid to the sponge-like material layer such that the sterilizing fluid is contained with the chambers; and
sealing the surfaces of the sponge-like material layer to substantially retain the sterilizing fluid within the sponge-like material layer.

45. A method of making a covering according to claim 44 wherein the covering comprises a glove.

46. A method of making a covering according to claim 44 wherein the covering comprises a condom.

47. A method of making a covering according to claim 44 wherein the sealing step comprises searing the surfaces of the sponge-like material layer such that the surfaces form a substantially uniform, continuous, non-porous barrier.

48. A method of making a covering according to claim 47 wherein the searing step comprises heating the surfaces such that a fluidized film of the sponge-like material forms along the surfaces and the solidifies.

49. A method of making a covering according to claim 44 wherein the sealing step comprises applying a sealant in a fluidized state to form a film of sealant on the surfaces of the sponge-like material layer and then solidifying the sealant such that the sealant forms a substantially uniform, continuous, non-porous barrier.

50. A method of making a covering according to claim 49 wherein the sealant application step comprises spraying the sealant.

51. A method of making a covering according to claim 49 wherein the sealant application step comprises dipping the sponge-like material layer into a vat of sealant.

52. A method of making a covering according to claim 47 wherein the thickness of covering is substantially in the range of one millimeter to five millimeters.

53. A method of making a covering according to claim 49 wherein the thickness of the covering is substantially in the range of one millimeter to five millimeters.

54. A method of making a covering according to claim 47 wherein the sterilizing fluid is capable of substantially immediately sterilizing microbes that cause AIDS.

55. A method of making a covering according to claim 49 wherein the sterilizing fluid is capable of substantially immediately sterilizing microbes that cause AIDS.

56. A method of making a covering according to claim 49 wherein the sealant comprises a plastic.

57. A method of making a covering according to claim 49 wherein the sealant comprises latex.

58. A method of making a covering for inhibiting the spread of a contagious disease comprising the steps of:
   providing a layer of flexible, absorbent material;
   providing a sterilizing fluid capable of substantially immediately sterilizing the microbes causing the disease;
   applying the sterilizing fluid to the absorbent material layer; and
   sealing the surfaces of the absorbent material layer to substantially retain the sterilizing fluid within the absorbent material layer.

59. A method of making a covering according to claim 58 wherein the covering comprises a glove.

60. A method of making a covering according to claim 58 wherein the covering comprises a condom.

61. A method of making a covering according to claim 58 wherein the fluid application step comprises substantially saturating the absorbent material layer with the sterilizing fluid.

62. Method of making a covering according to claim 58 wherein the sealing step comprises applying a sealant in a fluidized state to form a film of sealant on the surfaces of the absorbent material layer and then solidifying the sealant such that the sealant forms a substantially uniform, continuous, non-porous barrier.

63. A method of making a covering according to claim 62 wherein the sealant application step comprises spraying the sealant.

64. A method of making a covering according to claim 62 wherein the sealant application step comprises dipping the absorbent material layer into a vat of sealant.

65. A method of making a covering according to claim 58 wherein the thickness of the covering is substantially in the range of one millimeter to five millimeters.

66. A method of making a covering according to claim 62 wherein the thickness of the covering is substantially in the range of one millimeter to five millimeters.

67. A method of making a covering according to claim 58 wherein the sterilizing fluid is capable of substantially immediately sterilizing microbes that cause AIDS.

68. A method of making a covering according to claim 62 wherein the sterilizing fluid is capable of substantially immediately sterilizing microbes that cause AIDS.

69. A method of making a covering according to claim 62 wherein the sealant comprises a plastic.

70. A method of making a covering according to claim 62 wherein the sealant comprises latex.

71. A method of making a multi layered sheath for inhibiting the spread of a contagious disease to a person contacting the body fluid of a person infected with the disease, comprising the steps of:
   providing a first flexible, stretchable sheath having a thickness substantially in the range of one-half millimeter to four millimeters;
   providing a second flexible, stretchable sheath having a thickness substantially in the range of one-half millimeter to four millimeters and having a shape and configuration substantially identical to the first sheath and adapted to contain the first sheath conformingly therein;
   providing a sterilizing fluid capable of substantially immediately sterilizing the microbes causing the disease; and
   depositing the sterilizing fluid such that the sterilizing fluid is disposed in the region between the first sheath and the second sheath when the first sheath is conformingly contained within the second sheath and such that the sterilizing fluid forms a substantially uniform layer having a thickness substantially in the range of one-quarter millimeter to four millimeters and such that the sheaths substantially prevent the sterilizing fluid from seeping out of the region and through a sheath.

72. A method of making a multi layered sheath according to claim 71 wherein said multi layered sheath comprises a condom.

73. A method of making a multi layered sheath according to claim 71 wherein said multi layered sheath comprises a glove.

74. A method of making a multi layered sheath according to claim 71 wherein the sterilizing fluid is deposited by spraying the sterilizing fluid.

75. A method of making a multi layered sheath according to claim 71 wherein the sterilizing fluid is deposited by dipping the first sheath into a vat of the sterilizing fluid.

76. A covering for inhibiting the spread of a contagious disease to a person contacting the body fluid of a person infected with the disease comprising fluid-impermeable inner and outer surface layers and an intermediate layer comprising a plurality of discrete chambers encapsulating a sterilizing fluid capable of sterilizing microbes causing the disease substantially upon contact.

77. A covering according to claim 76 wherein the intermediate layer includes a plurality of strata each comprising a regular array of chambers containing the sterilizing fluid, the chambers in each stream being staggered relative to the chambers in an adjacent stratum.

78. A covering according to claim 77 wherein the intermediate layer comprises two strata of chambers.

79. A covering according to claim 77 wherein said chambers number substantially in the range of between fifty and five hundred.

80. A covering according to claim 77 wherein each chamber has a volume of less than substantially two cubic millimeters.

81. A covering according to claim 1 wherein said intermediate layer comprises an open cell sponge-like material possessing at least two hundred chambers each having a volume of less than substantially two cubic millimeters.

82. A covering according to claim 76 wherein the intermediate layer comprises an absorbent flexible material.

83. A covering according to claim 76 having a thickness substantially in the range of one millimeter to five millimeters.

84. A covering according to claim 76 in the form of a glove.

85. A covering according to claim 76 in the form of a condom.

86. A covering according to claim 85 wherein the chambers encapsulating the sterilizing fluid are contained only in the head or tip region of the condom.

* * * * *

UNITED STATES PATENT AND TRADEMARK OFFICE
CERTIFICATE OF CORRECTION

PATENT NO. : 4,919,966

DATED : April 24, 1990

INVENTOR(S) : Robin R.T. Shlenker

It is certified that error appears in the above-identified patent and that said Letters Patent is hereby corrected as shown below:

Col. 6, claim 81, line 1, "claim 1" should be --claim 76--.

Signed and Sealed this

Fourteenth Day of January, 1992

Attest:

HARRY F. MANBECK, JR.

*Attesting Officer*  *Commissioner of Patents and Trademarks*